(12) United States Patent
Charette et al.

(10) Patent No.: US 8,508,742 B2
(45) Date of Patent: Aug. 13, 2013

(54) INTEGRATED SHEAR-VERTICAL SURFACE ACOUSTIC WAVE AND SURFACE PLASMON RESONANCE SENSING DEVICE AND METHOD

(75) Inventors: Paul G Charette, Sherbrooke (CA); Alan Renaudin, Sherbrooke (CA); Vincent Chabot, Sherbrooke (CA); Etienne Grondin, Sherbrooke (CA); Vincent Aimez, Sherbrooke (CA)

(73) Assignee: Societe de Commercialisation des Produits de la Recherche Appliquee—Socpra Sciences et Genie S.E.C., Sherbrooke, Quebec (CA)

( * ) Notice: Subject to any disclaimer, the term of this patent is extended or adjusted under 35 U.S.C. 154(b) by 180 days.

(21) Appl. No.: 12/989,202

(22) PCT Filed: Apr. 23, 2009

(86) PCT No.: PCT/CA2009/000550
§ 371 (c)(1),
(2), (4) Date: Oct. 22, 2010

(87) PCT Pub. No.: WO2009/129628
PCT Pub. Date: Oct. 29, 2009

(65) Prior Publication Data
US 2011/0032528 A1   Feb. 10, 2011

Related U.S. Application Data

(60) Provisional application No. 61/071,340, filed on Apr. 23, 2008.

(51) Int. Cl.
*G01N 21/55* (2006.01)
*G01D 5/32* (2006.01)

(52) U.S. Cl.
USPC .............................. 356/445; 436/518; 73/655

(58) Field of Classification Search
USPC ..................... 356/445–448, 432–440; 435/6, 435/287.2, 7.1; 333/133, 193–196; 310/313 A, 310/313 D; 436/524; 73/655
See application file for complete search history.

(56) References Cited

U.S. PATENT DOCUMENTS 5,321,331 A * 6/1994 Baer et al. ................ 310/313 D
6,161,437 A   12/2000 Brennan et al.
(Continued)

FOREIGN PATENT DOCUMENTS

JP   2003-535349 A   11/2003
JP   2006-226942 A   8/2006

OTHER PUBLICATIONS

Written Opinion for PCT/CA2009/000550.
(Continued)

*Primary Examiner* — Hoa Pham
(74) *Attorney, Agent, or Firm* — Anglehart et al.

(57) ABSTRACT

A device and method detect a feature of a fluid or a target element in the fluid by contacting the fluid to a sensing surface on a substrate. A mechanical wave comprising shear-vertical wave components is propagated through the substrate to mix the fluid, conduct desorption of at least one non-target element from the sensing surface, and/or impede adsorption of the non-target element to the sensing surface. The feature of the fluid or the target element in the fluid is then detected on the sensing surface, wherein the detection is accelerated by the above-mentioned mixing of the fluid, desorption of at least one non-target element from the sensing surface, and/or impeding of the adsorption of the non-target element to the sensing surface.

16 Claims, 8 Drawing Sheets

(56) References Cited

U.S. PATENT DOCUMENTS

| | | | |
|---|---|---|---|
| 6,600,391 B2* | 7/2003 | Kadota et al. | 333/193 |
| 7,942,568 B1* | 5/2011 | Branch et al. | 366/127 |
| 2001/0055529 A1 | 12/2001 | Wixforth | |
| 2004/0101975 A1* | 5/2004 | Gauer | 436/518 |
| 2004/0251792 A1* | 12/2004 | Matsuda et al. | 310/364 |
| 2006/0000285 A1* | 1/2006 | Edmonson et al. | 73/649 |
| 2006/0019313 A1* | 1/2006 | Andersson et al. | 435/7.1 |
| 2006/0173636 A1 | 8/2006 | Friedt et al. | |
| 2007/0016378 A1* | 1/2007 | Andersson | 702/19 |
| 2008/0060438 A1* | 3/2008 | Shinbo et al. | 73/579 |
| 2008/0163688 A1* | 7/2008 | Wang et al. | 73/580 |
| 2008/0303378 A1* | 12/2008 | Lee et al. | 310/313 A |
| 2009/0195784 A1* | 8/2009 | Ogura et al. | 356/445 |
| 2009/0282902 A1* | 11/2009 | Warthoe | 73/64.53 |
| 2010/0128272 A1* | 5/2010 | Zong et al. | 356/445 |
| 2011/0122410 A1* | 5/2011 | Wang et al. | 356/369 |

OTHER PUBLICATIONS

International Search Report for PCT/CA2009/000550.

The first office action of Japan application 2011-505332 dated Apr. 2, 2013.

* cited by examiner

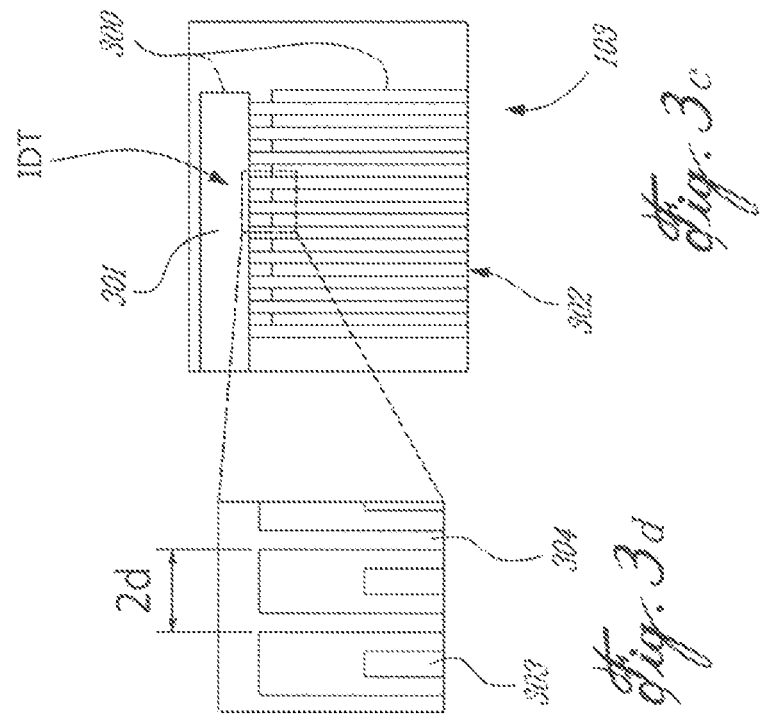
Fig. 3c
Fig. 3d
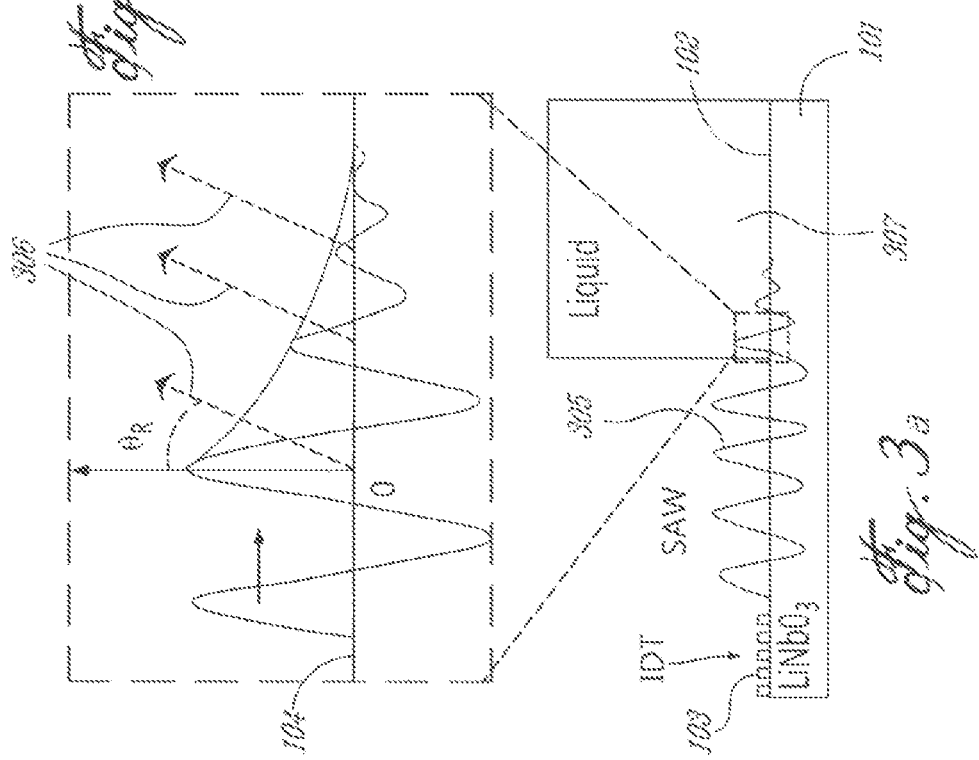
Fig. 3b
Fig. 3a

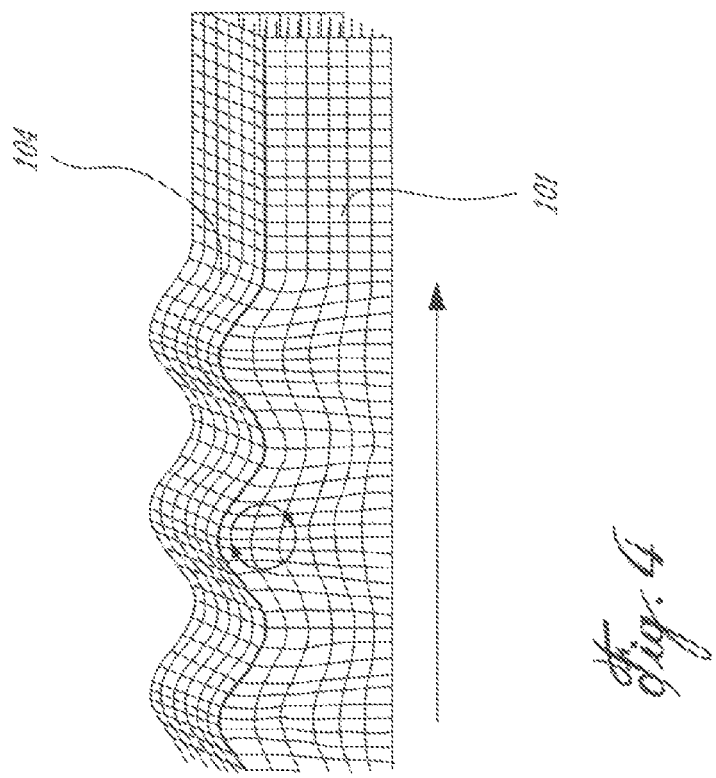
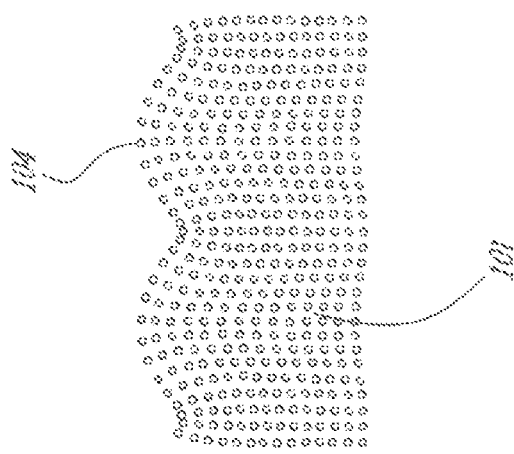
Fig. 4

INTEGRATED SHEAR-VERTICAL SURFACE ACOUSTIC WAVE AND SURFACE PLASMON RESONANCE SENSING DEVICE AND METHOD

FIELD OF THE INVENTION

The present invention generally relates to a device and method for detecting a feature of a fluid or a target element in the fluid while accelerating the detection.

BACKGROUND

In the medical and pharmaceutical industries, affinity biosensors for detecting and analyzing bio-molecular interactions, both for point-of-care applications and high throughput screening, have seen rapid development in recent years. Surface plasmon resonance (SPR) is widely used in these bio-sensing applications due to several attractive features such as:

SPR is label-free and, therefore, requires no fluorescent tagging;
SPR operates in real-time to measure reaction kinetics;
SPR can be implemented in parallel to perform high throughput screening and detect multiple target elements; and
SPR provides quantitative affinity measurements.

Several SPR biosensing systems are commercially available and have large established user bases. However, SPR biosensing systems are still the object of considerable efforts of research and development in both universities and the private sector. One of the reasons for this is that the medical and pharmaceutical researchers and industries require performance still higher than that the current SPR biosensing systems can deliver. Two challenges of SPR biosensing systems are the following:

To overcome sensitivity limitations due to non-specific adsorption; and
Efficient mixing at the microfluidic level for homogeneous and timely analysis.

DESCRIPTION OF THE DRAWINGS

In the appended drawings:

FIG. 3A is a schematic diagram showing propagation and coupling of a shear-vertical surface acoustic wave (SV-SAW; also called Rayleigh wave) into a fluid (liquid medium);

FIG. 3B is a zoomed view of FIG. 3A showing propagation and coupling of the SV-SAW wave in the liquid medium;

FIG. 3C is a top view of SV-SAW IDT (InterDigited Transducer) electrodes taken with an optical microscope;

FIG. 3D is a zoomed view showing a top view of a portion of the SV-SAW IDT electrodes of FIG. 3C;

FIG. 4 shows schematic diagrams illustrating the deformation of a piezoelectric substrate by a SV-SAW wave in a direction normal to a surface of the piezoelectric substrate to transfer energy from the SV-SAW wave into a fluid, both for accelerated microfluidic mixing and desorption;

DETAILED DESCRIPTION

Figure 1:
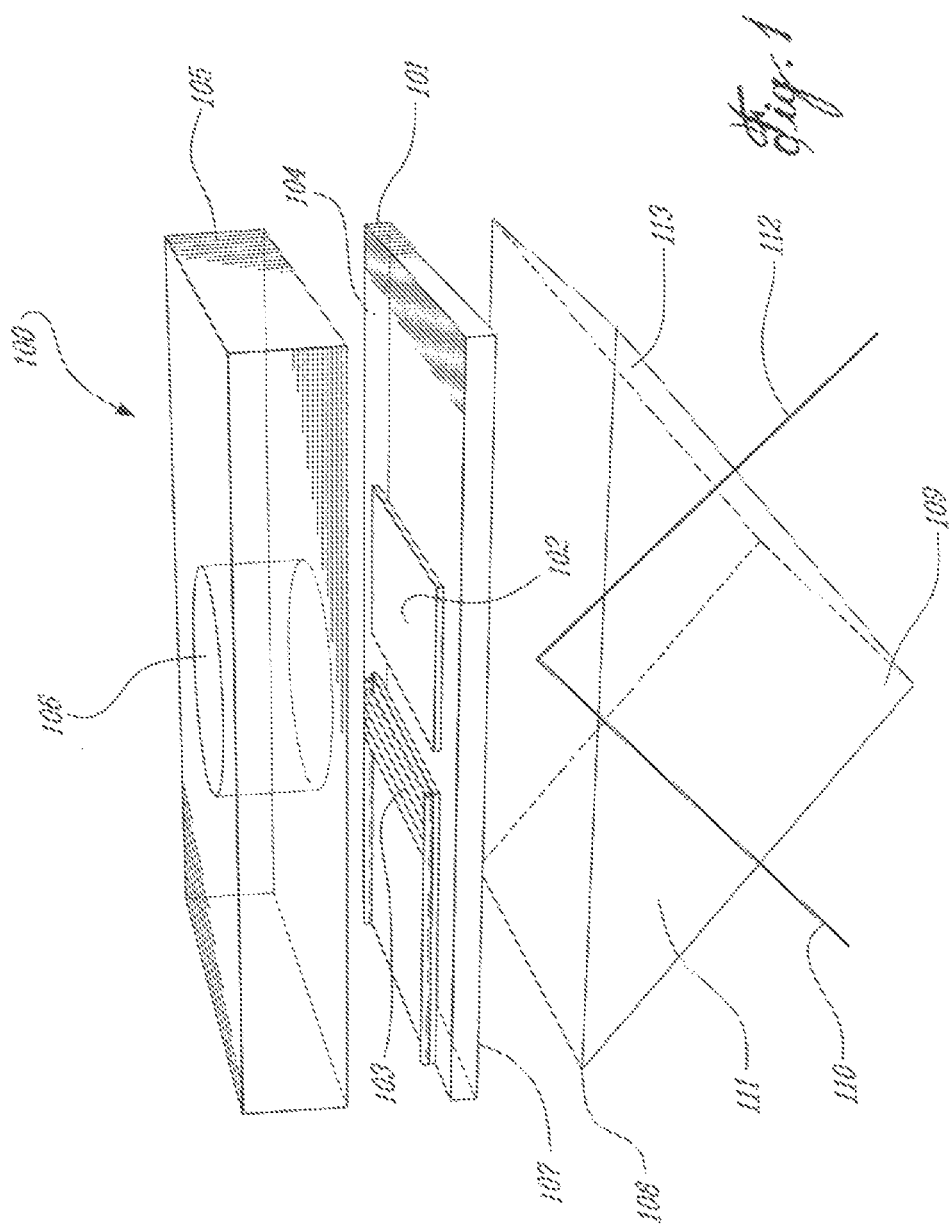
FIG. 1 is a schematic diagram of an embodiment of a SV-SAW/SPR sensing device according to the present invention.

According to a first non-restrictive illustrative embodiment of the present invention, there is provided a device for detecting a feature of a fluid or a target element in the a fluid while accelerating the detection, comprising:

a sensor mounted on a substrate and having a sensing surface for contacting the fluid and detecting the feature of the fluid or the target element in the fluid; and a mechanical wave generator mounted on the substrate for producing and propagating a mechanical wave through the substrate to mix the fluid, conduct desorption of at least one non-target element from the sensing surface, and/or impede adsorption of the at least one non-target element to the sensing surface in view of accelerating the detection, wherein the mechanical wave comprises shear-vertical wave components.

According to a second non-restrictive illustrative embodiment of the present invention, there is provided a method for detecting a feature of a fluid or a target element in the fluid while accelerating the detection, comprising:

contacting the fluid to a sensing surface on a substrate;

propagating a mechanical wave through the substrate to mix the fluid, conduct desorption of at least one non-target element from the sensing surface, and/or impede adsorption of the at least one non-target element to the sensing surface, wherein propagating the mechanical wave comprises producing shear-vertical wave components; and detecting on the sensing surface the feature of the fluid or the target element in the fluid, wherein mixing the fluid, conducting desorption of the at least one non-target element from the sensing surface, and/or impeding adsorption of the at least one non-target element to the sensing surface accelerates the detection.

The foregoing and other objects, advantages and features of the present invention will become more apparent upon reading of the following non-restrictive description of illustrative embodiments thereof, given as example only with reference to the accompanying drawings.

More specifically, the following disclosure describes an example of implementation of the present invention, in which SV-SAW and SPR are integrated on a common piezoelectric substrate to address the two (2) above mentioned challenges:

Reduction in or removal of (desorption) non-target element(s) (for example parasitic bio-molecules) bound to the SPR sensing surface due to non-specific adsorption, using SV-SAW waves (also called Rayleigh waves); and
Microfluidic mixing by "acoustic streaming" also using SV-SAW waves.

SV-SAW and SPR integrated on a common piezoelectric substrate lead to improved microfluidic assays for detecting and identifying a target element (for example pathogens, protein biomarkers, genetic biomarkers, etc.) with greater accuracy, selectivity, and speed in multiple applications such as drug discovery, infectious disease detection, environmental testing, medical diagnostics, etc.

Non-specific adsorption is a non-covalent (weak) binding, due to mechanisms such as physisorption, of at least one non-target element, for example a bio-molecule other than the target element to the SPR sensing surface. At best, non-specific adsorption causes false positive readings and/or errors in quantitative estimates of the concentration of the target element. At worst, measurements of the target element can be completely obscured by the non-target element. Reduction in, or forced removal (desorption) of weakly bound parasitic molecules (non-target element(s)) from the SPR sensing surface by SV-SAW will increase the measurement signal-to-noise ratio.

Also, to minimize the quantity of expensive reagents being used, modern sensing devices and methods use microfluidics, in which micro- or nano-liter sized fluid volumes are pumped through small channels having cross-sectional dimensions ranging from hundreds to tens of microns. A challenge with microfluidics is to efficiently mix reagents because the fluid flow at such small scales is laminar. The main consequence of laminar flow is a relatively slow diffusion-limited mixing and surface organization effects that lead to non-linear ligand/analyte binding rates (adsorption isotherms). For example, some common surface biochemistry reactions are left to incubate over a period of hours for completion. Accelerated microfluidic mixing using SV-SAW will considerably increase the throughput of SPR sensing devices and other similar sensing methods.

An example of SV-SAW/SPR sensing device according to the present invention will now be described with reference to FIG. 1. It should be kept in mind that the SV-SAW/SPR sensing device can be constructed in a plurality of different ways.

Referring to FIG. 1, the SV-SAW/SPR sensing device 100 comprises a piezoelectric substrate 101. As illustrated in FIG. 1, both the SPR sensing surface 102 and SV-SAW IDT electrodes 103 are integrated to the common piezoelectric substrate 101. More specifically, both the SV-SAW IDT electrodes 103 and SPR sensing surface 102 are thin metal films deposited on a surface 104 of the common piezoelectric substrate 101. Several methods including micro-fabrication methods can be used to produce the thin metal films such as photolithography, lift-off, wet etching, etc. The thin metal films forming the SV-SAW IDT electrodes 103 and the SPR sensing surface 102 can be fabricated simultaneously in a single step or separately in different steps.

An additional layer 105, for example made of polymer material, is deposited on the surface 104 of the common piezoelectric substrate 101 over the SV-SAW IDT electrodes 103 and the SPR sensing surface 102 to form a fluidic well 106 to receive fluid containing the target element. As can be seen in FIG. 1, the SPR sensing surface 102 is exposed at the bottom of the fluidic well 106.

On a surface 107 of the common piezoelectric substrate 101 opposite to surface 104 is applied a surface 108 of a prism 109 generally triangular or semi circular in cross section. SPR excitation light 110 propagates along a SPR excitation light path through a surface 111 of the prism 109, the prism 109 and the common piezoelectric substrate 101 to reach the thin metal film forming the SPR sensing surface 102. The reflected light 112 follows a light path from the thin metal film forming the SPR sensing surface 102 through the common piezoelectric substrate 101, the prism 109 and a surface 113 of the prism 109. The prism is secured to the surface 107 of the substrate 101 with a substance adapted to prevent light alteration between the prism 109 and the surface 107. In fact, the SPR excitation and reflected light paths are coupled to the thin metal layer forming the SPR sensing surface 102 through the prism 109 and the common piezoelectric substrate 101. Those of ordinary skill in the art will know that a piezoelectric substrate 101 made for example of $LiNbO_3$ will be substantially transparent to the SPR visible and near-infrared excitation and reflected light.

Figure 2:
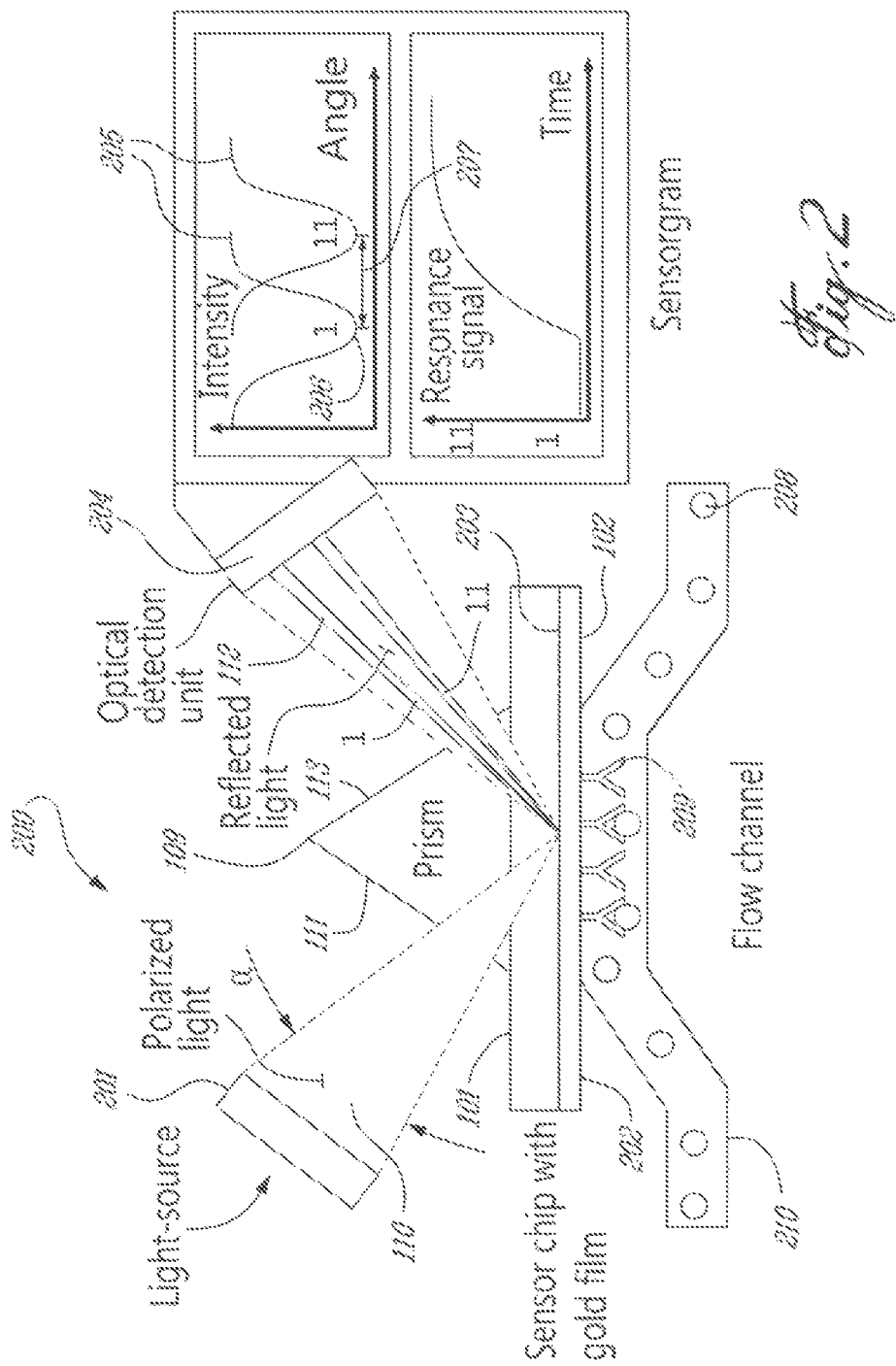
FIG. 2 is a schematic diagram of a Kretschmann SPR configuration.

For example, the attachment of a target element in the fluid contained in the fluidic well 106 to ligands bound to the SPR sensing surface 102 can be monitored using SPR in the Kretschmann configuration. The principle of operation of the Kretschmann SPR configuration is shown in FIG. 2. More specifically, FIG. 2 is a schematic diagram of a Kretschmann SPR configuration Referring to FIG. 2, SPR excitation polarized light 110 is produced by a light source 201 over a given spread of incidence angles $\alpha$. To produce the given spread of incidence angles $\alpha$, the light source 201 may use, for example, mechanical scanning or dispersive optics (not shown).

The SPR excitation polarized light 110 propagates along the SPR excitation light path through the surface 111 of the prism 109, the prism 109 and the common piezoelectric substrate 101 to reach the thin metal film 202, for example a gold film, forming the SPR sensing surface 102. The reflected light 112 follows the light path from the thin metal film 202 through the common piezoelectric substrate 101, the prism 109 and the surface 113 of the prism 109. In fact, the SPR excitation and reflected light paths are coupled to the thin metal layer 202 forming the SPR sensing surface 102 through the prism 109 and the common piezoelectric surface 101.

The capture of a target element by a ligand on the sensing surface 102 produces changes in the surface plasmon coupling conditions in the thin metal film 202. At a specific critical angle, which is dependent upon the index of refraction in the dielectric medium in contact with the SPR sensing surface 102 of the thin metal film 202, the incident excitation polarized light 110 will couple strongly into the surface plasmons propagating on the metallic sensing surface 102 and a minimum amplitude will be observed in the reflected light 112 detected through an optical detector 204. Capture of a target element such as 208 by a ligands such as 209 can be tracked by detecting a shift 207 in the angular position of the minimum 206 of the reflectivity curve 205 (Intensity of reflected light versus angle of propagation of the reflected light). Minimum point I corresponds to the angular position of the minimum 206 of the reflectivity curve 205 without binding of the target element, and minimum point II corresponds to the angular position of the minimum 206 of the reflectivity curve 205 with binding of the target element.

The SPR configuration of FIG. 2 is inverted (prism on top, fluid on the bottom) relative to the configuration of FIG. 1. The fluidic subsystems are also different. In FIG. 1, the fluidic subsystem is a fluidic well 106 while in FIG. 2 the fluidic subsystem is a flow-through channel 210. Fluid flow through the channel 210 wherein the target element such as 209 is bound by the ligand such as 208 on the sensing surface 102. Of course, the flow-through channel 210 is designed to allow the fluid flowing therein to come into contact with the SPR sensing surface 102. However, the SPR working principle and functionality in both cases are identical; this demonstrates that the SPR and fluidics aspects can be implemented in the form of a plurality of different embodiments.

SPR is believed to be otherwise well known to those of ordinary skill in the art and, accordingly, will not be further described in the present specification.

As indicated in the foregoing description, shear-vertical surface acoustic wave (SV-SAW) interdigited transducer (IDT) electrodes 103 of FIG. 1 are mounted on the surface 104 of the common piezoelectric substrate 101 to generate SV-SAW (also called Rayleigh waves). SV-SAW are mechanical vibrations that propagate at the surface 104 of the piezoelectric substrate 101. They are generated using thin-film metal IDT electrodes such as 103 deposited on the surface 104 of the piezoelectric substrate 101.

Figure 5:
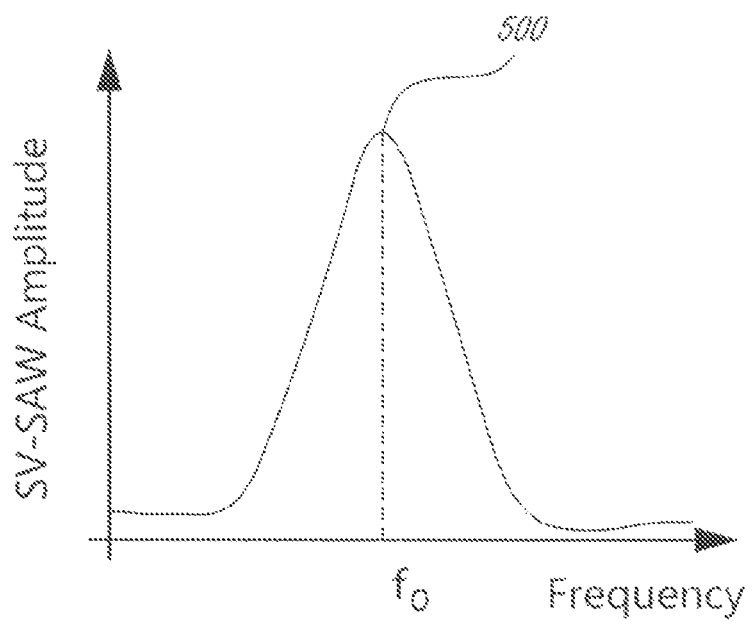
FIG. 5 is a graph showing the SV-SAW amplitude versus the electrical excitation frequency, wherein the maximum amplitude is obtained at the resonance frequency, $f_0$.

Referring to FIG. 3A, an IDT 103 comprises a metallic comb-like structure disposed on the surface 104 of the piezoelectric substrate made for example $LiNbO_3$. More specifically, the interdigited transducer (IDT) 103 of FIG. 3C comprises a first comb-like electrode 301 and a second comb-like electrode 302 (both shown in part only in FIG. 3C). The comb-like electrodes 301 and 302 define respective fingers 303 and 304 alternating with each other and intermeshed with each other to form the IDT electrode structure of FIGS. 3C and 3D. The width and spacing of the alternating, intermeshed fingers 303 and 304 are adjusted to obtain the desired wavelength for the SV-SAW waves. In the same manner, the length of the alternating, intermeshed fingers 303 and 304 is adjusted to obtain the desired width of the train of the SV-SAW waves. An electrical signal, for example a pulsed electrical signal, is applied across the comb-like electrodes 301 and 302 and therefore across the fingers 303 and 304. The electrical signal applied across the comb-like electrodes 301 and 302 is also applied at the resonance frequency $f_0$ (see 500 in FIG. 5) for a maximum SV-SAW amplitude across sections of the piezoelectric material of the substrate 101 to deform (contract and extend) these portions of the piezoelectric material and convert the electrical energy into mechanical energy, more specifically into SV-SAW waves propagating at the surface 104 of the common piezoelectric substrate 101 in a direction perpendicular to the fingers 303 and 304. The IDT electrodes 103 generate SV-SAW waves with equal amplitudes in both directions and hence are bidirectional.

FIG. 3A is a schematic diagram showing generation of the SV-SAW waves by means of the SV-SAW IDT electrodes 103 and the propagation of the SV-SAW waves 305 on the surface 104 of the common piezoelectric substrate 101, for example a piezoelectric substrate made of $LiNbO_3$, and the SPR sensing surface 104. The zoomed view of FIG. 3B illustrates the transfer (arrows 306) of acoustic energy into the fluid 307 that conducts desorption and mixing because of a radiation pressure 306 created in the fluid.

Since the SPR sensing surface 102 and the SV-SAW IDT electrodes 103 are both integrated to the surface 104 of the common piezoelectric substrate 101, the SV-SAW waves 305 propagate on the surface 104 of the common piezoelectric substrate 101 towards the fluidic well 106, as seen on FIG. 1, or flow-through channel 210, as seen on FIG. 2. More specifically, the SV-SAW waves will induce mixing of the fluid in the fluidic well 106 or the flow-through channel 210 (acoustic streaming) and desorption of non-target element(s), for example unwanted parasitic bio-molecules, from the SPR sensing surface 102.

As illustrated in FIG. 4, SV-SAW or Rayleigh waves deform the surface 104 of the piezoelectric substrate 101 in a direction normal to the surface 104, like rolling waves on an ocean and accordingly transfers energy (see arrows 306 of FIG. 3B) from the SV-SAW waves into the fluid either in the fluidic well 106 or the flow-through channel 210, both for accelerated microfluidic mixing and desorption. This will accelerate microfluidic mixing and desorption to improve sensitivity and throughput of SPR sensing device and method.

Analysis of experimental results has confirmed accelerated mixing and reaction times and removal (desorption) of non-specifically bound elements such as parasitic bio-molecules. SPR has successfully been performed on a piezoelectric substrate made for example of $LiNbO_3$. By conducting desorption to remove non-target element(s), for example non-specifically bound chemical species from the SPR sensing surface 102, SV-SAW increases the signal-to-noise ratio of the SPR measurements.

Experiments have also confirmed that a SPR metal sensing surface coated with a thin film of $SiO_2$ (10 nm thickness) appropriate for aminosilane-based chemistry could be used to perform SPR on a $LiNbO_3$ substrate.

Figure 6:
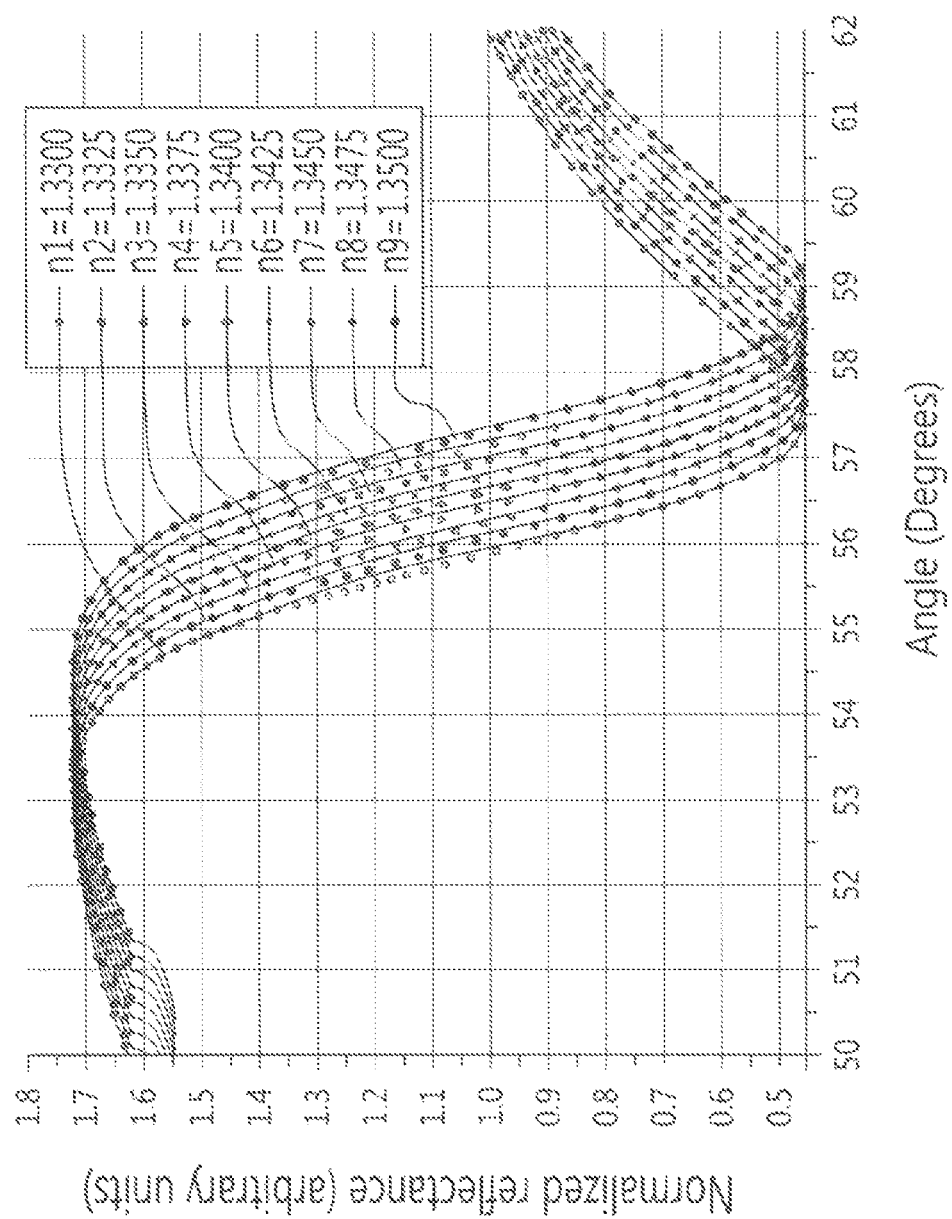
FIG. 6 is a graph showing SPR reflectivity curves for nine (9) fluids (liquids) with different optical refractive indices ($\eta_1$=1.3300; $\eta_2$=1.3325; $\eta_3$=1.3350; $\eta_4$=1.3375; $\eta_5$=1.3400; $\eta_6$=1.3425; $\eta_7$=1.3450; $\eta_8$=1.3475 and $\eta_9$=1.3500)

FIG. 6 is a graph showing SPR reflectivity curves using a $LiNbO_3$-based substrate for nine (9) fluids (liquids) with different optical refractive indices ($\eta_1=1.3300$; $\eta_2=1.3325$; $\eta_3=1.3350$; $\eta_4=1.3375$; $\eta_6=1.3400$; $\eta_6=1.3425$; $\eta_7=1.3450$; $\eta_8=1.3475$ and $\eta_9=1.3500$). More specifically, FIG. 6 shows shifting of the SPR reflectivity curves to the right (larger angles of minimum reflectivity) with increasing refractive index, using a set of fluids with pre-calibrated values of refractive index.

Figure 7A:
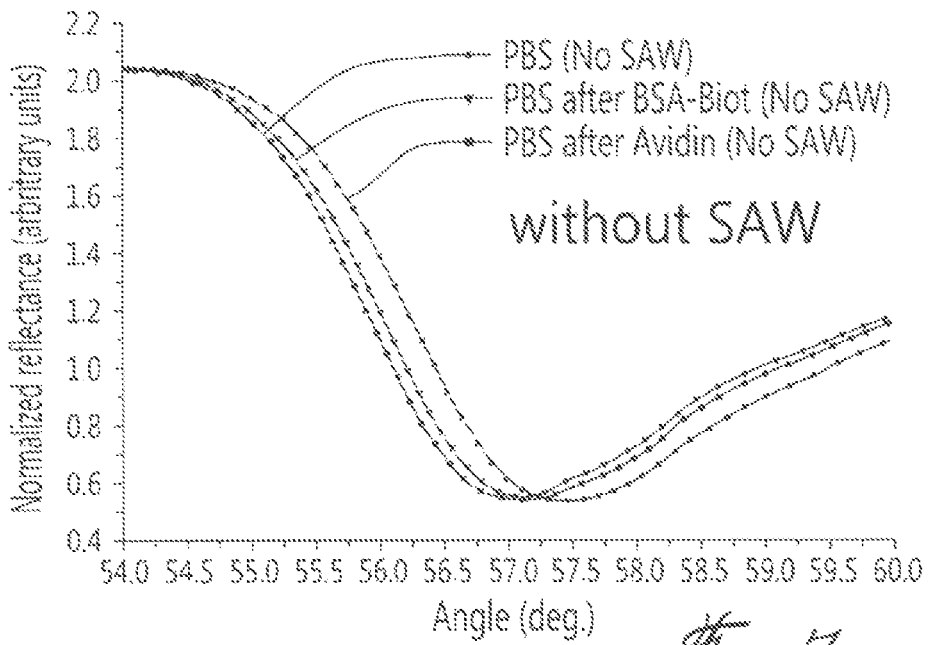
FIG. 7A is a graph showing SPR reflectivity curves obtained without SV-SAW for adsorption of biotinylated bovine serum albumin (BSA-Biotin) to a SPR sensing surface followed by covalent binding of avidin to the biotin.
Figure 7B:
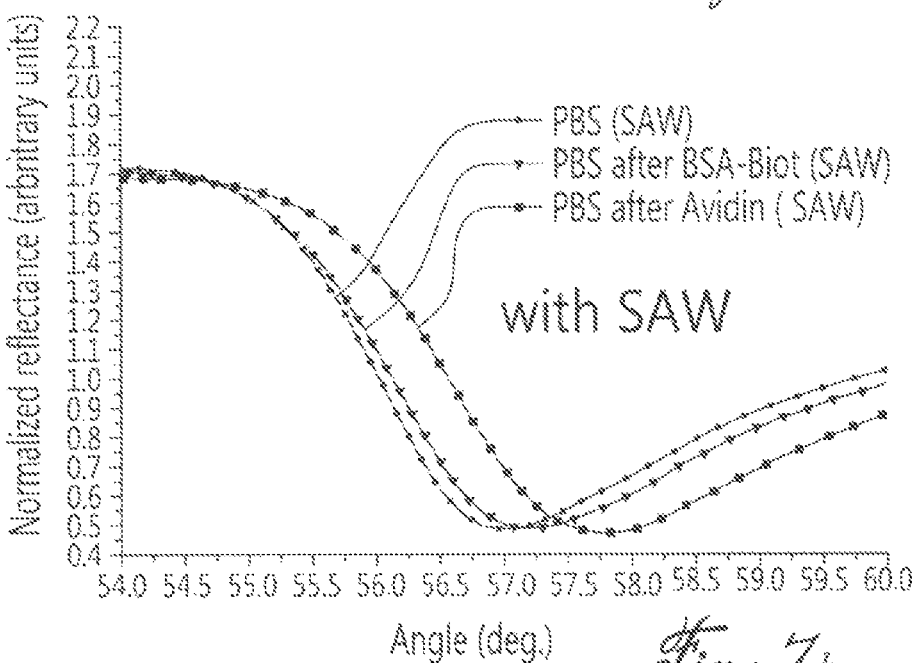
FIG. 7B is a graph showing SPR reflectivity curves obtained with SV-SAW for adsorption of biotinylated bovine serum albumin (BSA-Biotin) to the SPR sensing surface followed by covalent binding of avidin to the biotin.

The SPR performance of the $LiNbO_3$-based chip was also experimented with a standard affinity assay: biotin-avidin in a phosphate buffer (PBS), as shown in the graph of FIG. 7A, where a biotinylated bovine serum albumin (BSA) complex is adsorbed on the SPR sensing surface, followed by the introduction of avidin which has a strong affinity for biotin. The increased mixing efficiency under the action of SV-SAW is shown in the graph of FIG. 7B. Under identical experimental conditions over the same time interval, the graph of FIG. 7B clearly shows that more material (avidin) has bound to the BSA-biotin complex on the surface, as demonstrated by the greater shift of the right-most SPR curve.

Figure 8:
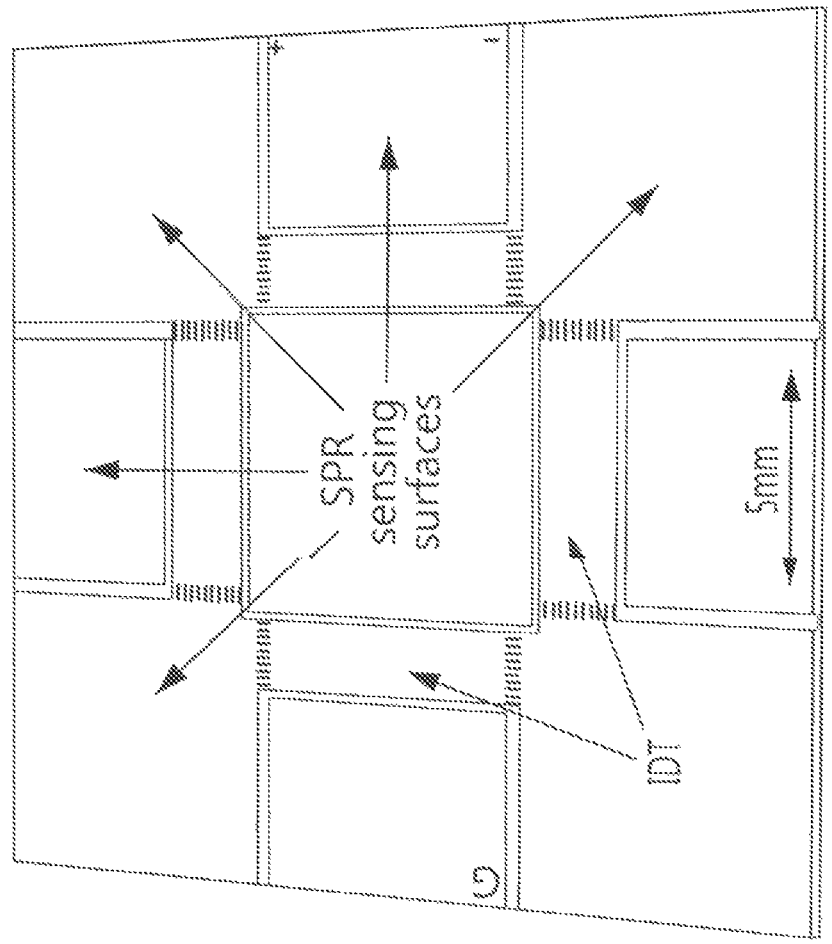
FIG. 8 is a photograph of an embodiment of a SV-SAW/SPR sensing device comprising SV-SAW IDT and SPR metal electrodes on a piezoelectric substrate.

FIG. 8 is a photograph of an example of SV-SAW/SPR sensing device chip showing an embodiment of layout of the IDT and SPR metal sensing surfaces on the common piezoelectric substrate.

Embodiment Variations:

1. Though SV-SAW can be used for removing non-target element(s) non-specifically bound to the SPR sensing surface (desorption) after a chemical reaction has completed, SV-SAW can also be used to impede non-specific absorption during the chemical reaction, thus dynamically increasing the efficiency of attachment of the target element(s) by covalent bonding (specific) to the ligand(s) on the SPR sensing surface.

2. The SV-SAW waves transmit mechanical energy into the fluid, both by mechanical deformation of the surface of the piezoelectric substrate but also via the electrical field. This creates turbulent flow in the fluid which accelerates mixing and chemical reaction, compared to slow mixing and reaction times due to diffusion alone.

3. The SV-SAW/SPR device and method according to the present invention can be controlled using electronics and software under various configurations.

4. The SPR sensing area may comprise a single sensing area or multiple sensing areas, such as in an array configuration used in SPR-imaging (SPRi).

5. The common substrate can be a piezoelectric substrate as described hereinabove or a non-piezoelectric substrate coated with a piezoelectric film made for example of polycrystalline piezoelectric material (ZnO, $BiTaO_3$, PZT, $PbZrO_3$, AlN, etc.), single crystal materials ($LiTaO_3$), quartz, langasite ($La_3Ga_5SiO_{14}$), or $GaPO_4$ (example: Lee, et al. *Integrated ZnO surface acoustic wave microfluidic and biosensor system*, in IEEE International Electron Devices Meeting—IEDM '07, Washington, D.C., USA, 2007).

6. The SPR configuration is not limited to the Kretschmann configuration: other SPR configurations such as that using waveguides (Krol et al., U.S. Pat. No. 6,829,073 B1) and/or diffractive optical elements (Knoll et al. Surface plasmon-field-enhanced diffraction sensor. US Patent Application 2006/0194346 A1 and European Patent Application EP20050003435., and Thirstrup et. al. *Diffractive optical coupling element for surface plasmon resonance sensors*. Sensors and Actuators B (Chemical), 2004, 100(3): p298-308) could also be used.

7. The SPR configuration can use angle-scanning systems (mechanically-scanned or parallel systems using a non-collimated beam), angle-dispersive systems, wavelength-scanned systems (tunable wavelength source or parallel chromatically dispersive system), hybrid systems (simultaneous angle and wavelength scanning systems), as well as near-resonance optical phase scanning systems.

8. The SV-SAW IDT electrodes and SPR sensing surfaces can be fabricated from various metals, gold being the most common. Other examples include silver, copper, aluminium, palladium, etc. A coating may be applied to the metal to protect its surface and/or to facilitate organic chemistry functionalization. A typical approach for coating is to use a thin film of silicon dioxide, although the use of other coating materials can also be envisaged.

9. The IDT electrodes are not limited to rectilinear electrodes and can be fabricated in a wide variety of geometries depending on the kind of SV-SAW propagation desired such as bulk, surface skimming bulk, etc. (for example: Wu, et al. *Actuating and detecting of microdroplet using slanted finger interdigital transducers*. J. of Applied Physics, 2005, 98(2): p024903-7). The frequency of the pulse excitation of the IDT electrodes can typically be of the order of between 10 to 1000 MHz, although such frequency can be adapted to the particular microfluidic system.

10. In terms of manufacturability, both the SPR sensing surface and SV-SAW IDT electrodes involve metal deposition requiring resolutions that are easily achievable with low-cost lithography commercial fabrication methods.

11. It is possible to use SV-SAW configurations comprising either a single or multiple IDTs, depending on the requirements of the particular application. Also, the IDTs can be used for fluid droplet actuation and pulse/echo fluid droplet localization (Renaudin, et al. *Surface acoustic wave two-dimensional transport and location of microdroplets using echo signal*. Journal of Applied Physics, 2006, 100(11): p116101-1).

12. The fluidic subsystem may comprise a number of possible embodiments: fluidic droplet, fluid in a well, fluid in a flow-through microfluidic channel, etc.

13. The term fluid may encompass pure liquids, mixtures, suspensions, colloids and dispersions as well as liquids in which solid material, for example, biological materials (such as cells, DNA, proteins, molecules, drugs, chemical compounds, nucleic acids, peptides, etc.) or carbon nanotubes are contained.

14. Although foregoing examples pertain to detection of bioassays or biological material, the present invention applies equally well to detection of inorganic elements such as inorganic molecules or inorganic substances.

15. Many arrangements of SV-SAW IDT electrodes and SPR sensing surface on the common substrate are possible of which FIG. 8 is only an example. FIG. 8 is not to be understood as superceding the generality of the foregoing description.

16. Although the integrated SV-SAW/SPR device and method has been described herein above for detecting biomolecules in a fluid, it should be understood that the integrated SV-SAW/SPR device and method can also be used to perform a wide variety of studies, for example the study of cell attachment, cell migration, drug permeability and solubility, virus detection and protein secretion, carbon nanotubes (CNTs) adsorption.

17. Although the foregoing description only explicitly mentions SPR combined with SV-SAW, it should be kept in mind that it is possible to use any sensing technology other than SPR that uses thin metal films on the same substrate as the SV-SAW IDT, such as resonant waveguide grating (RWG) sensing (K. Tiefenthaler and W. Lukosz, "*Sensitivity of grating couplers as integrated-optical chemical sensors*," Journal of the Optical Society of America, 6(2), 1989, p. 209-220) or microcalorimetry (A. Bourque-Viens, V. Aimez, A. Taberner, P. Nielsen and P. G. Charette. "*Modelling and experimental validation of thin-film effects in thermopile-based microscale calorimeters*," Sensors and Actuators A: Physical, 150(2), 2009, p. 199-206).

18. Although the foregoing specification describes SV-SAW, it should be kept in mind that SV-SAW can be replaced by any other technology capable of producing a mechanical wave propagating at the surface of a substrate, the mechanical wave comprising shear-vertical components sufficient to adequately mix a fluid for the purposes of the application of concern.

19. The method for detecting a feature of a fluid or a target element in the fluid can be used for the purpose of analyzing binding kinetics (such as affinity constants, dissociation constant, equilibrium conditions, time constants, etc.) in assays involving analytes such as DNA, proteins, antibody/antigens, pathogens, and other biomolecules.

Although the present invention has been described hereinabove by way of non-restrictive illustrative embodiments thereof, these embodiments can be modified at will within the scope of the appended claims without departing from the spirit and nature of the present invention.

What is claimed is:

1. A device for detecting a feature of a fluid or a target element in the fluid while accelerating the detection, comprising:
    a sensor mounted on a substrate and having a sensing surface for contacting the fluid and detecting the feature of the fluid or the target element in the fluid; and
    a mechanical wave generator mounted on the substrate for producing and propagating a mechanical wave through the substrate to mix the fluid in view of accelerating said detection, wherein the mechanical wave comprises shear-vertical wave components, the substrate is a piezoelectric substrate, the sensing surface and the mechanical wave generator are on a common surface of the piezoelectric substrate, and the sensing surface comprises a surface plasmon resonance sensing surface.

2. A device for detecting a feature of a fluid or a target element in the fluid as defined in claim 1, wherein the mechanical wave generator comprises a shear-vertical surface acoustic wave generator.

3. A device for detecting a feature of a fluid or a target element in the fluid as defined in claim 2, wherein the shear-vertical surface acoustic wave generator comprises interdigited transducer electrodes on the common surface of the substrate.

4. A device for detecting a feature of a fluid or a target element in the fluid as defined in claim 3, wherein the interdigited transducer electrodes are made of a film of metal on the common surface of the piezoelectric substrate.

5. A device for detecting a feature of a fluid or a target element in the fluid as defined in claim 1, wherein the substrate comprises a non-piezoelectric substrate coated with a piezoelectric film.

6. A device for detecting a feature of a fluid or a target element in the fluid as defined in claim 1, comprising a fluidic well to contain the fluid.

7. A device for detecting a feature of a fluid or a target element in the fluid as defined in claim 1, comprising a flow-through channel in which the fluid flows.

8. A device for detecting a feature of a fluid or a target element in the fluid as defined in claim 1, wherein the sensor comprises:
   a film of metal having a first surface applied to a first surface of the substrate and defining a surface plasmon resonance sensing surface opposite to substrate; and
   a light-propagating prism applied to a second surface of the substrate opposite to the first surface of said substrate, wherein surface plasmon resonance excitation light propagates toward the first surface of the metal film through the prism and the substrate and light is reflected from the first surface of the metal film and propagates through the substrate and the prism.

9. A device for detecting a feature of a fluid or a target element in the fluid as defined in claim 1, wherein the substrate is made of $LiNbO_3$.

10. A method for detecting a feature of a fluid or a target element in the fluid while accelerating the detection, comprising:
    contacting the fluid to a surface plasmon resonance (SPR) sensing surface on a piezoelectric substrate;
    propagating a mechanical wave through the substrate to mix the fluid, wherein propagating the mechanical wave comprises producing shear-vertical wave components; and
    detecting, using SPR, on the sensing surface the feature of the fluid or the target element in the fluid, wherein mixing the fluid accelerates the detection.

11. A method for detecting a feature of a fluid or a target element in the fluid as defined in claim 10, comprising containing the fluid into a fluidic well.

12. A method for detecting a feature of a fluid or a target element in the fluid as defined in claim 10, comprising flowing the fluid through a flow-through channel.

13. A method for detecting a feature of a fluid or a target element in the fluid as defined in claim 10, comprising:
    applying a film of metal having a first surface to a first surface of the substrate, the metal film defining a surface plasmon resonance sensing surface opposite to the first surface of the metal film;
    applying a light-propagating prism to a second surface of the substrate opposite to the first surface of said substrate;
    propagating surface plasmon resonance excitation light toward the first surface of the metal film through the prism and the substrate; and
    propagating light reflected from the first surface of the metal film through the substrate and the prism.

14. A method for detecting a feature of a fluid or a target element in the fluid as defined in claim 10, for the purpose of analyzing binding kinetics in assays involving analytes.

15. A method for detecting a feature of a fluid or a target element in the fluid as defined in claim 14, wherein the binding kinetics are selected from the group consisting of affinity constants, dissociation constant, equilibrium conditions and time constants.

16. A method for detecting a feature of a fluid or a target element in the fluid as defined in claim 14, wherein the analytes are selected from the group consisting of DNA, proteins, antibody/antigens, pathogens, and other biomolecules.

\* \* \* \* \*